United States Patent
Tseng et al.

(10) Patent No.: US 7,875,246 B2
(45) Date of Patent: Jan. 25, 2011

(54) FILTER COLUMN MODULE

(75) Inventors: Ching-Tai Tseng, Beidou Township, Changhua County (TW); Tung-Liang Huang, Hsinchu (TW)

(73) Assignee: Industrial Technology Research Institute, Hsinchu (TW)

(*) Notice: Subject to any disclaimer, the term of this patent is extended or adjusted under 35 U.S.C. 154(b) by 911 days.

(21) Appl. No.: 11/293,087

(22) Filed: Dec. 5, 2005

(65) Prior Publication Data

US 2006/0131226 A1 Jun. 22, 2006

(30) Foreign Application Priority Data

Dec. 17, 2004 (TW) .............................. 93139330 A

(51) Int. Cl.
 *B01D 63/00* (2006.01)
 *C02F 1/44* (2006.01)
(52) U.S. Cl. .................... 422/101; 422/104; 210/321.6; 210/321.72; 210/321.84
(58) Field of Classification Search .............. 210/321.6, 210/321.72, 321.75, 321.84, 406, 419, 439, 210/450, 454, 459; 422/101, 104
See application file for complete search history.

(56) References Cited

U.S. PATENT DOCUMENTS

| | | | | |
|---|---|---|---|---|
| 4,510,058 A | * | 4/1985 | Cais et al. | 210/657 |
| 4,675,110 A | * | 6/1987 | Fay | 210/436 |
| 4,777,021 A | * | 10/1988 | Wertz et al. | 422/101 |
| 5,124,041 A | * | 6/1992 | Sheer et al. | 210/641 |
| 5,549,816 A | * | 8/1996 | Harp et al. | 210/120 |
| 5,591,345 A | * | 1/1997 | Engelen et al. | 210/640 |
| 5,601,711 A | * | 2/1997 | Sklar et al. | 210/238 |
| 5,733,449 A | * | 3/1998 | Bowers et al. | 210/321.6 |
| 5,998,214 A | * | 12/1999 | Guirguis | 436/165 |
| 6,506,167 B1 | * | 1/2003 | Ishimito et al. | 600/577 |
| 2004/0005246 A1 | * | 1/2004 | Efthimiadis et al. | 422/99 |

* cited by examiner

*Primary Examiner*—Tony G Soohoo
*Assistant Examiner*—David C Mellon
(74) *Attorney, Agent, or Firm*—Bacon & Thomas, PLLC

(57) ABSTRACT

A filter column module is disclosed, which has an upper column having a top opening, and a protruding bottom shell. The bottom shell has a plurality of apertures, and a diameter smaller than that of the upper column. A lower column has a support at the bottom and an opening that accommodates the protruding bottom shell of the upper column. The support partially contacts the protruding bottom shell of the upper column, and liquid or air can pass through the support. A filter is placed between the protruding bottom shell of the upper column and the support of the lower column.

18 Claims, 5 Drawing Sheets

FILTER COLUMN MODULE

BACKGROUND OF THE INVENTION

1. Field of the Invention

The present invention relates to a filter column module, and more particularly, to a filter column module for bio-sample concentration and purification.

2. Description of the Related Art

For bio-sample concentration and purification, the recovering rates of samples are a very important issue. By using centrifugal technologies, higher recovering rates can be achieved, but this technology is not suitable for automatic, high throughput systems. As a result, the precious biological samples may remain in the isolating or purifying apparatus, and hence lead to a deficiency in sample volumes.

Membrane separation technologies have been developed for automatic sample concentration and purification, which may use a single filter tube or a multi-pore filter plate to fasten the membrane by way of heat bonding, ultrasonic bonding or friction bonding. However, the above-mentioned methods are used in centrifugal systems, and multi-pore filter plates are not suitable for small quantities of samples.

Therefore, it is desirable to provide a filter column module to mitigate and/or obviate the aforementioned problems.

SUMMARY OF THE INVENTION

The filter column module of the present invention utilizes a vacuum pumping system instead of a centrifugal system, and so may be applied in an automatic apparatus. Additionally, the filter column module of the present invention can increase the sample recovering rate.

The filter column module of the present invention comprises:

an upper column having a top opening and a protruding bottom shell, wherein the bottom shell has a plurality of apertures, and the protruding bottom shell has a diameter smaller than that of the upper column;

a lower column having a support at a bottom and an opening, the opening of the lower column accommodating the protruding bottom shell of the upper column, wherein the support partially contacts the protruding bottom shell of the upper column, and liquid or air can pass through the support; and a filter, placed between the protruding bottom shell of the upper column and the support of the lower column.

For operational convenience, the filter column module further comprises a loading base with fixing troughs, and the fixing troughs can be arranged in n×m arrays, wherein the n and m are integers not less than 1 such as 96 trough arrays, 192 trough arrays, or 384 trough arrays. The filter column module of the present invention is preferably operated by means of vacuum pumping, so an exhaust channel of the loading base is preferably provided. Furthermore, in order to ensure high efficiency of the vacuum pump, an elastic O-ring can be placed between the upper column and the lower column, and between the lower column and the loading base to improve the hermetic seal.

The filter can be any filter used in the prior art, such as a molecular sieve membrane, which can block bio-samples, such as nucleic acid, and only allow water, gas, small molecular salts, etc. to pass through. The protruding bottom shell of the upper column may have any shape, but in order to ensure that the filter adheres to the protruding bottom shell without wrinkling, the protruding bottom shell is preferably formed in a stepped-shaped, U-shaped or V-shaped design, and each surface of the design may have at least one open hole. Correspondingly, the top opening of the lower column may be formed in a stepped-shaped, U-shaped or V shaped design to match the protruding bottom shell of the upper column.

To improve sealing between the different elements, the upper column and the lower column may have different diameters to provide a sliding combination. The largest diameter of the protruding bottom shell of the upper column is preferably smaller than the top opening of the lower column, so that the protruding bottom shell of the upper column can be placed within the top opening of the lower column. After insertion of the lower column, the support for the lower column partially contacts the protruding bottom shell of the upper column, and a filter can be placed between the lower column support and the protruding bottom shell of the upper column.

An elastic O-ring can be placed between each element assembly, such as between the upper column and the lower column, and the lower column and the loading base. In order to prevent the upper column and the lower column from sliding off of each other, at least one positioning element is placed on the lower column; the positioning element may be positioning points, positioning pins or positioning blocks.

The loading base of the filter column module may be connected to a pump to provide vacuum pumping. To increase tightness between the upper column, the filter and the lower column, the protruding bottom shell of the upper column may have different shaped edges, such as wave-shaped edges or saw tooth-shaped edges.

Other objects, advantages, and novel features of the invention will become more apparent from the following detailed description when taken in conjunction with the accompanying drawings.

DETAILED DESCRIPTION OF THE PREFERRED EMBODIMENT

The filter column module of the present invention utilizes friction to fasten a filter between two columns, and, in order to avoid cross-contamination between different samples, the present invention utilizes a single filter column, a single filter membrane and 96-well arrays. Also, an automatic apparatus is operated in coordination to achieve higher recovering rates of concentration and purification for a biological sample.

Embodiment 1

Figure 1A:
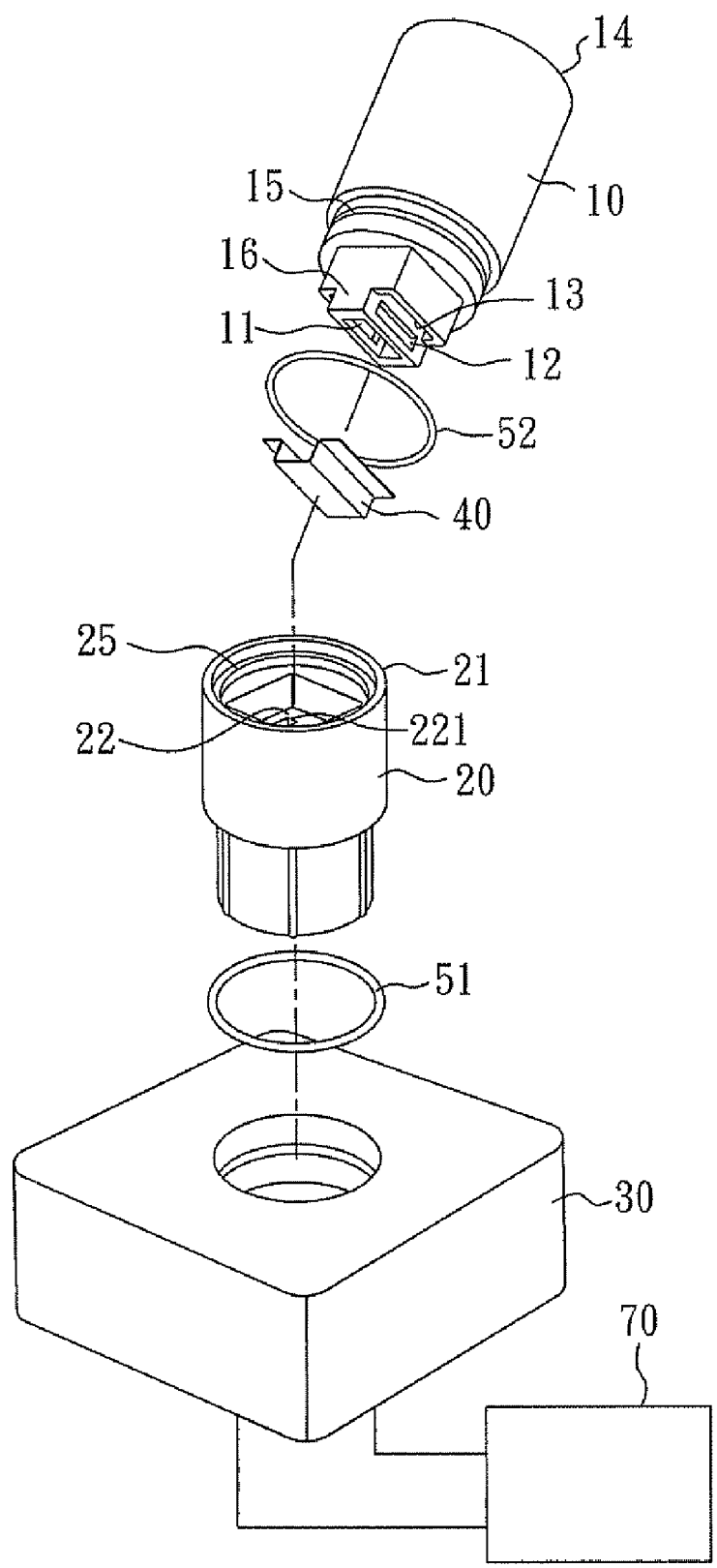
FIG. 1A is a schematic diagram of a filter column module according to the present invention.

Please refer to FIG. 1A. A filter column module of the present invention has an upper column 10 and a lower column 20. For convenience, a loading base 30 can be added for emplacement of the lower column 20 to stabilize the entire module.

The upper column 10 comprises a top opening 14 for the input of samples, and a protruding bottom shell 16 that has a plurality of apertures 11, 12, 13 and two additional apertures (not shown) facing the apertures 12, 13 on each surface of protruding bottom shell 16. Consequently, as shown in the drawing, all five bottom faces on the stepped-shaped protruding bottom shell 16 of the upper column 10 are permeable, which increases the efficiency of the filter.

With an equal volume of a liquid sample, the height of the liquid surface in the upper column 10 presented in the embodiment with a stepped configuration is greater than that of a traditional round-bottom filter tube, which can reduce residues forming at the bottom and provide higher sample recovering rates.

The lower column 20 and the upper column 10 can be inserted into each other, and an opening 21 of the lower column 20 can snugly hold the protruding bottom shell 16 of the upper column 10. A sieve membrane 40 is placed between the lower column 20 and the upper column 10, which is a molecular sieve membrane in this embodiment. The sieve membrane 40 can be fixed when the lower column 20 is mounted onto the upper column 10, or may be glued onto the protruding bottom shell of the upper column 10 before being combined with the lower column 20. The sieve membrane 40 may be folded into a stepped shape to match the shape of the protruding bottom shell of the upper column 10, which prevents the sieve membrane 40 wrinkling and increases permeability.

When combining the elements, an elastic O-ring can be utilized to provide better sealing between each element for complete vacuum pumping. As shown in FIG. 1, the sieve membrane 40 is placed on the protruding bottom shell of the upper column 10. An elastic O-ring 52 is inserted between the lower column 20 and the upper column 10. A protrusion 15 on the upper column 10, and a groove 25 on the lower column 20 are used to fasten the columns together. Next, the assembled filter column is placed in a fixing trough on the loading base 30, and an elastic O-ring 51 is also provided between the filter column and the loading base 30.

The bottom of the lower column 20 has a support 22 with at least one hole 221; when the upper column and the lower column are combined, the support 22 partially contacts the protruding bottom shell of the upper column to prevent the sieve membrane 40 from rupturing under the vacuum pressure.

Figure 1B:
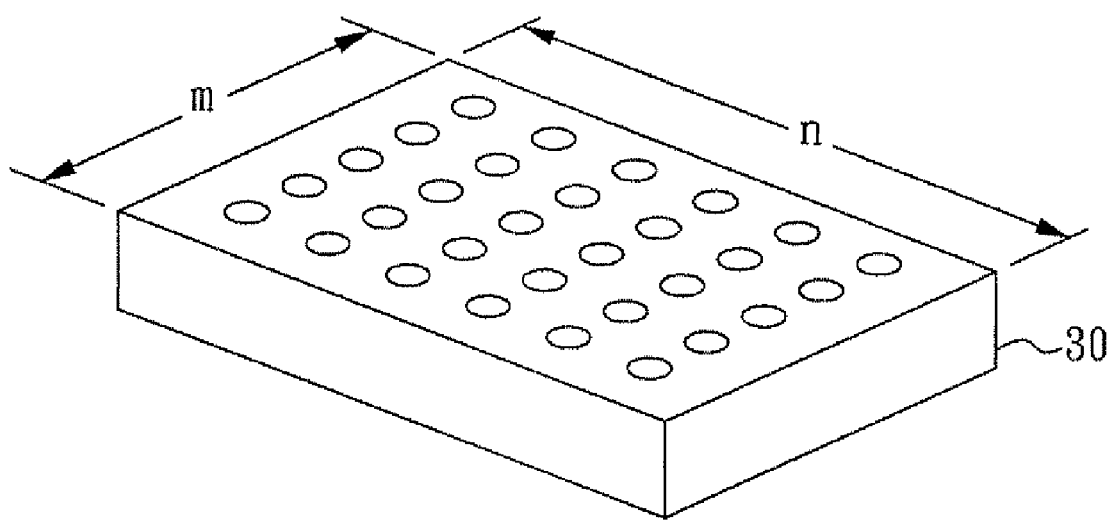
FIG. 1B is a diagrammatic illustration of a loading base having n×m fixing trough array.

For the filtering process, all of the elements are assembled together, and a sample is introduced at the top opening 14 of the upper column 10 to directly flow into the apertures 11, 12, 13 of the protruding bottom shell 16 (because of the sieve membrane 40, the sample will not flow through the protruding bottom shell 16). After the filter column module is connected to a vacuum pump 70 through the loading base 30, the filter column module is placed under a vacuum; excess water and small molecular salts in the sample drain through the sieve membrane 40 into the lower column 20, and eventually into the loading base 30 to concentrate the sample. As shown in FIG. 1A, the loading base 30 has one fixing trough. However, the loading base 30 also may have nxm fixing trough array, as shown in FIG. 1B, in which the array nxm may be 96, 196 or 384.

Embodiment 2

Figure 2:
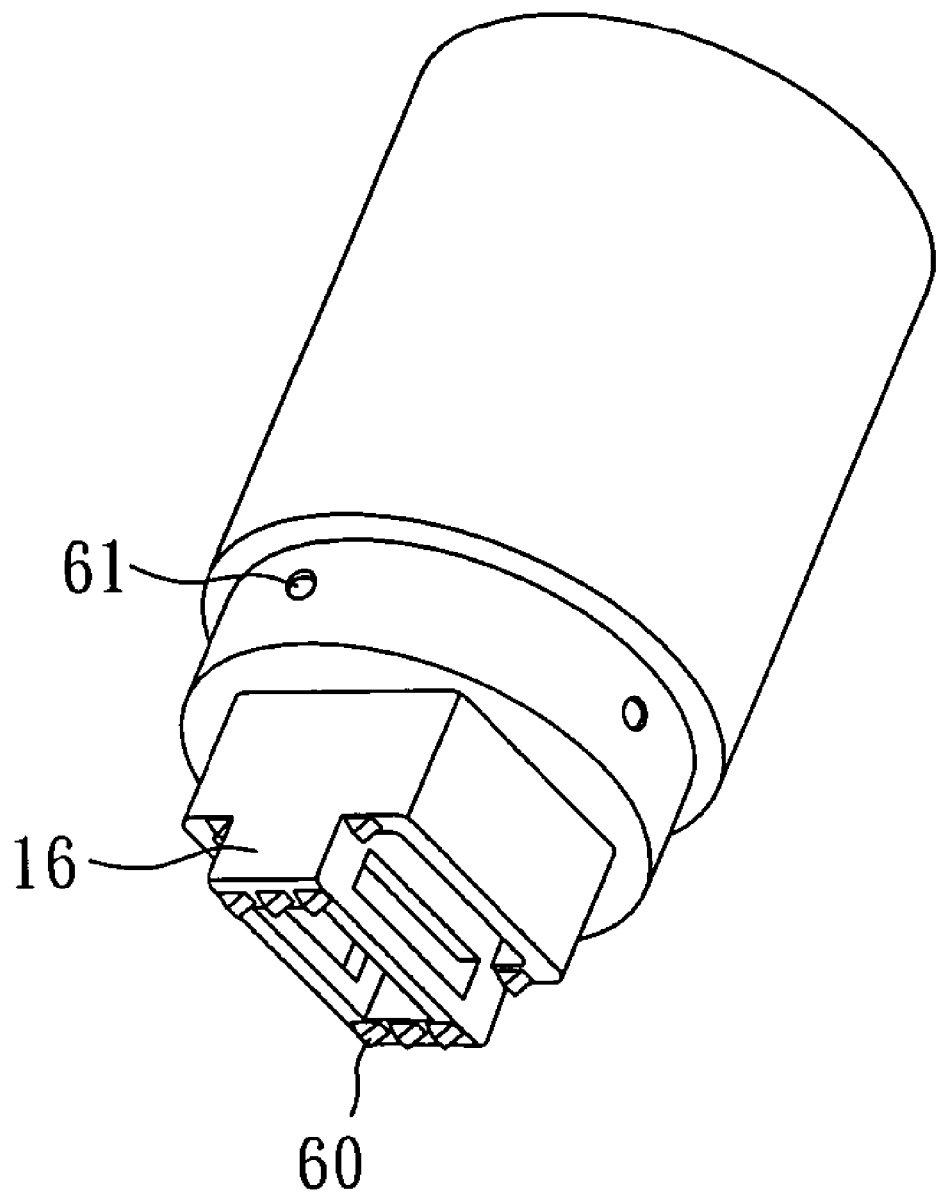
FIG. 2 shows the structure of an upper column in an embodiment according to the present invention.

FIG. 2 shows an upper filter column with a saw-toothed edge. By utilizing the saw-toothed edge 60 on the protruding bottom shell 16, the sieve membrane 40 is provided a better seal at the edge of the column. The edge of the column may have other profiles, such as an undulating shape. Additionally, the upper column and the lower column may also be fastened together by way of a plurality of positioning points 61.

Embodiment 3

Figure 3:
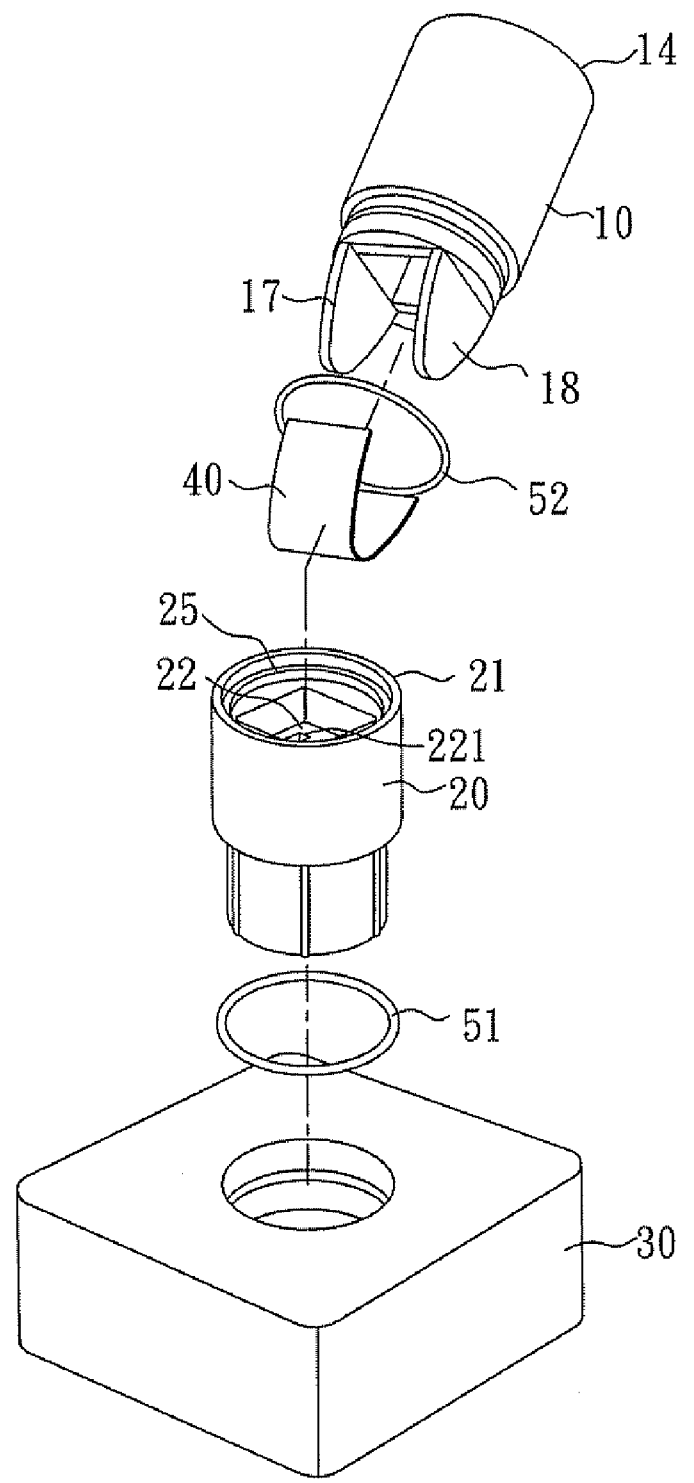
FIG. 3 shows the structure of an upper column in another embodiment according to the present invention.

As shown in FIG. 3, a bottom of the upper column 10 may have two U-shaped supports 17, 18. These two U-shaped supports 17, 18 impart a friction force on the sieve membrane 40 when the upper column 10 and the lower column 20 are combined together. The bottom of the lower column 20 is a support 22 with at least one hole 221. When the upper column and the lower column are combined together, the support 22 partially contacts the protruding bottom shell of the upper column to prevent the sieve membrane 40 from breaking under the vacuum pumping.

An elastic O-ring 52 may be inserted between the lower column 20 and the upper column 10, and a protrusion 15 on the upper column 10 and a groove 25 on the lower column 20 can be mated together. Next, the assembled filter column can be placed in a fixing trough on the base 30, and an elastic O-ring 51 can also be disposed between the column and the base 30.

Embodiment 4

Figure 4:
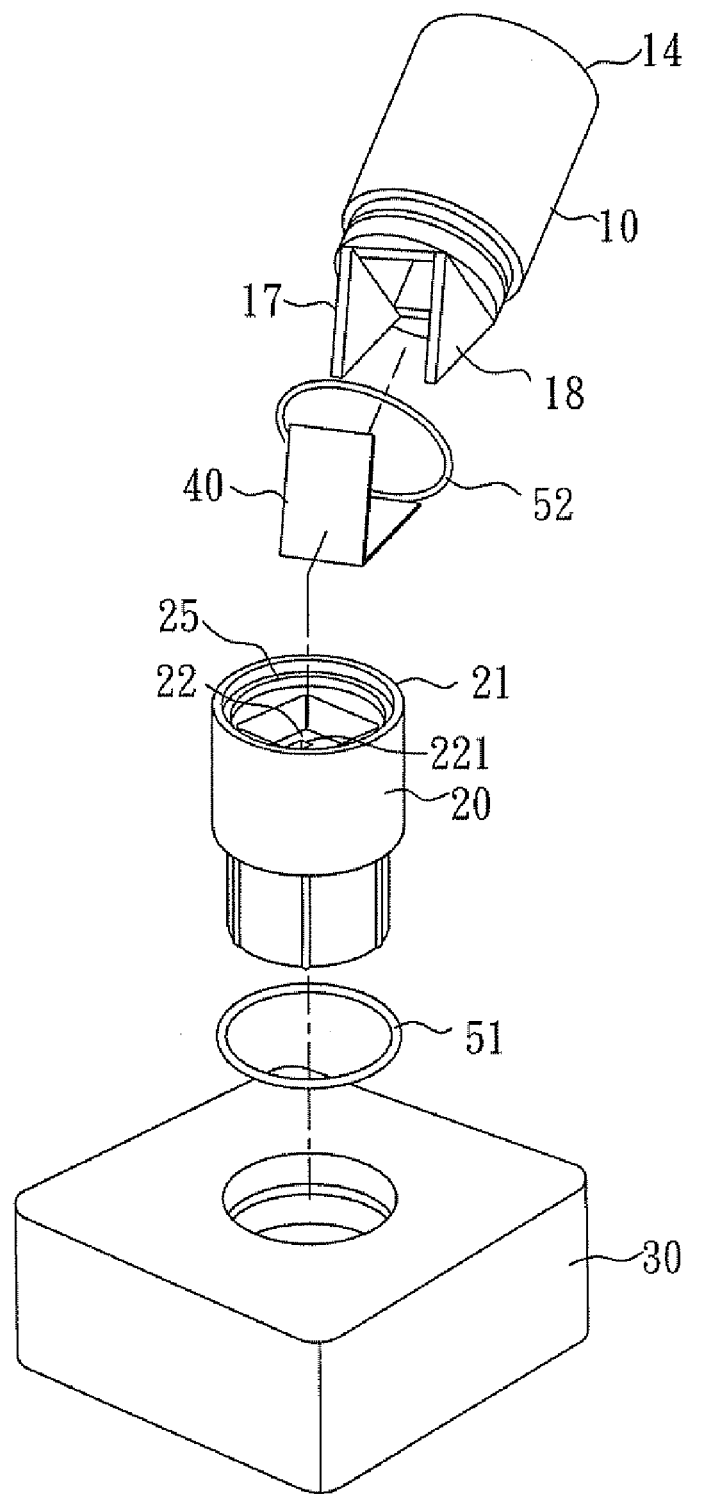
FIG. 4 shows the structure of an upper column in another embodiment according to the present invention.

The filter column module according to the present embodiment is the same as that illustrated in Embodiment 3, except that the supports 17, 18 and the sieve membrane 40 are V-shaped, as shown in FIG. 4.

Although the present invention has been explained in relation to its preferred embodiment, it is to be understood that many other possible modifications and variations can be made without departing from the spirit and scope of the invention as hereinafter claimed.

What is claimed is:

1. A filter column module comprising:
    an upper column having a top opening and a protruding bottom shell, wherein the protruding bottom shell is stepped-shaped having a plurality of step surfaces, each of the step surfaces having at least one aperture configured to allow a sample to pass through the protruding bottom shell;
    a lower column having a support at a bottom and an opening, the opening of the lower column being stepped-shaped to correspond with and receive the protruding bottom shell of the upper column, wherein the support partially contacts the protruding bottom shell of the upper column; and
    a filter, placed between the protruding bottom shell of the upper column and the support of the lower column, and conforming to the stepped-shape of the protruding bottom shell, the filter being supported against the support, wherein the support has at least one hole to allow liquid or air filtered by the filter to pass through the support.

2. The filter column module as claimed in claim 1, further comprising a loading base having nxm fixing trough arrays.

3. The filter column module as claimed in claim 2, wherein the n and m are integers not less than 1.

4. The filter column module as claimed in claim 2, wherein the loading base has 96 fixing trough arrays.

5. The filter column module as claimed in claim 2, wherein the loading base has 192 fixing trough arrays.

6. The filter column module as claimed in claim 2, wherein the loading base has 384 fixing trough arrays.

7. The filter column module as claimed in claim 1, wherein a flexible ring is disposed between the upper column and the lower column.

8. The filter column module as claimed in claim 2, wherein a flexible ring is disposed between the lower column and the loading base.

9. The filter column module as claimed in claim 1, wherein the filter is frictionally fastened between the upper column and the lower column.

10. The filter column module as claimed in claim 9, wherein the protruding bottom shell of the upper column has a plurality of protrusions for increasing friction between the filter, the upper column and the lower column.

11. The filter column module as claimed in claim 1, wherein the filter is a molecular sieve membrane.

12. The filter column module as claimed in claim 1, wherein the upper column and the lower column have different diameters for a sliding combination.

13. The filter column module as claimed in claim 1, wherein the protruding bottom shell of the upper column is inserted into the opening of the lower column.

14. The filter column module as claimed in claim 12, wherein at least one positioning element is placed between the upper column and the lower column.

15. The filter column module as claimed in claim 14, wherein the positioning element is a positioning point.

16. The filter column module as claimed in claim 2, wherein the loading base is connected to vacuum pump.

17. The filter column module as claimed in claim 1, wherein the protruding bottom shell of the upper column has a plurality of protrusions for increasing friction between the filter, the upper column and the lower column.

18. The filter column module as claimed in claim 1, wherein the filter is folded in a stepped-shape corresponding to the stepped-shaped protruding bottom shell.

* * * * *